US010327924B2

(12) United States Patent
Kelly

(10) Patent No.: US 10,327,924 B2
(45) Date of Patent: Jun. 25, 2019

(54) BRIDGING STENT GRAFT WITH COMBINATION BALLOON EXPANDABLE AND SELF-EXPANDABLE STENTS AND METHODS FOR USE

(71) Applicant: Sanford Health, Sioux Falls, SD (US)

(72) Inventor: Patrick W. Kelly, Sioux Falls, SD (US)

(73) Assignee: Sanford Health, Sioux Falls, SD (US)

(*) Notice: Subject to any disclaimer, the term of this patent is extended or adjusted under 35 U.S.C. 154(b) by 0 days.

(21) Appl. No.: 15/214,165

(22) Filed: Jul. 19, 2016

(65) Prior Publication Data

US 2017/0014248 A1 Jan. 19, 2017

Related U.S. Application Data

(60) Provisional application No. 62/194,258, filed on Jul. 19, 2015.

(51) Int. Cl.
*A61F 2/86* (2013.01)
*A61F 2/95* (2013.01)
(Continued)

(52) U.S. Cl.
CPC .......... *A61F 2/86* (2013.01); *A61F 2/07* (2013.01); *A61F 2/90* (2013.01); *A61F 2/95* (2013.01);
(Continued)

(58) Field of Classification Search
CPC ........... A61F 2/82–2002/91591; A61F 2/06–2002/077; A61F 2250/0018
(Continued)

(56) References Cited

U.S. PATENT DOCUMENTS 5,383,892 A * 1/1995 Cardon ............... A61F 2/90
606/198
5,747,128 A * 5/1998 Campbell ......... A61B 17/12131
428/35.7
(Continued)

FOREIGN PATENT DOCUMENTS

EP 1493401 A1 1/2005
WO 00/41649 A1 7/2000
WO 01/35864 A1 5/2001

OTHER PUBLICATIONS

International Search Report for corresponding PCT Application No. PCT/US2016/042988 dated Oct. 13, 2016.

*Primary Examiner* — Ryan J. Severson
*Assistant Examiner* — Charles M Wei
(74) *Attorney, Agent, or Firm* — McDonnell Boehnen Hulbert & Berghoff LLP

(57) ABSTRACT

The present disclosure provides a stent graft defining a lumen having a first end and a second end, the stent graft comprising (a) a first portion at the first end of the stent graft having a first diameter and a first length, wherein a first stent structure of the first portion is balloon-expandable, (b) a second portion of the stent graft having a second diameter and a second length, wherein a second stent structure of the second portion is self-expanding, (c) a breakable restraint configured to be coupled to the second portion in a pre-deployment state and decoupled from the second portion in a deployed state, and (d) a third portion at the second end of the stent graft has a third diameter and a third length, wherein a third stent structure of the third portion is balloon-expandable.

19 Claims, 3 Drawing Sheets

(51) Int. Cl.
*A61F 2/07* (2013.01)
*A61F 2/90* (2013.01)
*A61M 5/14* (2006.01)
*A61F 2/82* (2013.01)

(52) U.S. Cl.
CPC ......... *A61M 5/14* (2013.01); *A61F 2002/072* (2013.01); *A61F 2002/828* (2013.01); *A61F 2230/0069* (2013.01); *A61F 2250/0048* (2013.01); *A61F 2250/0071* (2013.01)

(58) Field of Classification Search
USPC .................... 623/1.11–1.13, 1.15, 1.16, 1.23
See application file for complete search history.

(56) References Cited

U.S. PATENT DOCUMENTS

| | | | | |
|---|---|---|---|---|
| 5,776,161 A * | 7/1998 | Globerman | ............... | A61F 2/90 606/192 |
| 5,827,321 A * | 10/1998 | Roubin | ............... | A61F 2/91 606/195 |
| 5,843,158 A * | 12/1998 | Lenker | ............... | A61F 2/07 623/1.13 |
| 6,071,298 A * | 6/2000 | Lashinski | ............... | A61F 2/90 606/194 |
| 6,156,064 A * | 12/2000 | Chouinard | ............... | A61F 2/07 623/1.44 |
| 6,238,430 B1 * | 5/2001 | Klumb | ............... | A61F 2/88 606/108 |
| 6,264,690 B1 * | 7/2001 | Von Oepen | ............... | A61F 2/82 623/1.15 |
| 6,273,910 B1 * | 8/2001 | Limon | ............... | A61F 2/91 623/1.15 |
| 6,280,465 B1 * | 8/2001 | Cryer | ............... | A61F 2/95 623/1.11 |
| 6,306,162 B1 * | 10/2001 | Patel | ............... | A61F 2/958 623/1.11 |
| 6,325,825 B1 * | 12/2001 | Kula | ............... | A61F 2/91 623/1.15 |
| 6,336,937 B1 * | 1/2002 | Vonesh | ............... | A61F 2/07 623/1.13 |
| 6,350,277 B1 * | 2/2002 | Kocur | ............... | A61F 2/90 623/1.11 |
| 6,468,302 B2 * | 10/2002 | Cox | ............... | A61F 2/91 623/1.15 |
| 6,569,191 B1 * | 5/2003 | Hogan | ............... | A61F 2/90 623/1.11 |
| 6,585,758 B1 * | 7/2003 | Chouinard | ............... | A61F 2/91 623/1.16 |
| 6,945,994 B2 * | 9/2005 | Austin | ............... | A61F 2/91 623/1.15 |
| 8,764,813 B2 * | 7/2014 | Jantzen | ............... | A61F 2/07 623/1.13 |
| 2001/0049551 A1 * | 12/2001 | Tseng | ............... | A61F 2/07 623/1.15 |
| 2001/0056299 A1 * | 12/2001 | Thompson | ............... | A61F 2/90 623/1.53 |
| 2003/0195609 A1 * | 10/2003 | Berenstein | ............... | A61F 2/856 623/1.15 |
| 2005/0004647 A1 * | 1/2005 | Bassoe | ............... | A61F 2/958 623/1.11 |
| 2007/0270939 A1 * | 11/2007 | Hood | ............... | A61F 2/82 623/1.22 |

\* cited by examiner

BRIDGING STENT GRAFT WITH COMBINATION BALLOON EXPANDABLE AND SELF-EXPANDABLE STENTS AND METHODS FOR USE

RELATED APPLICATIONS

This application claims priority to U.S. Provisional Application No. 62/194,258 entitled "Bridging Stent Graft with Combination Balloon Expandable and Self-Expandable Stents and Methods for Use," filed on Jul. 19, 2015, which is hereby incorporated by reference in its entirety.

BACKGROUND THE INVENTION

Aneurysms are characterized as a bulging in an artery that results in a thinning of the arterial wall that can lead to rupture. An aneurysm rupture is a potentially life threatening condition. To repair an aneurysm, the surgeon would traditionally remove the diseased arterial tissue and replace it with a cloth replacement tube. This approach is extremely invasive and not an option for some patients.

Endovascular techniques make use of catheters to deliver a stent graft to the diseased site by gaining arterial access through small incisions in the groin or arm. The stent graft bridges the aneurysmal segment of the artery by firmly anchoring in two adjacent healthy segments of arterial tissue. The stent graft is held open by a metal scaffold or "stent" and uses a cloth cover to form a conduit for blood flow that keeps the blood pressure from reaching the diseased tissue. Traditionally, this device has worked well for aneurysms that are in the straight segment of the descending thoracic aorta or in the infrarenal aorta. But stent grafts have been less effective in areas of the branches of the aortic arch, branches of the descending thoracic aorta, or near the iliac branch. In order to repair these branched areas, bridging stents may be utilized. Bridging stents are relatively small diameter stent grafts that span from the main body stent graft to the native branch vessel. These bridging stents have unique requirements from covered stents used for other purposes.

Self-expanding stents can be desirable for complex aneurysm repair for their flexibility. Such self-expanding stents can make bends as they change directions from the main body stent graft to the target branch vessel, and may also exhibit kink resistance. As such, in the event that the aneurysm remodels, the self-expanding stent may avoid kinking and ultimately occluding in addition to allowing some compliance to the remodeling. However, self-expanding stents require an outer sheath or catheter to be pulled back in order to deploy. With no or partial apposition in the branch vessel, the pulling force can pull the stent from the target. This can be problematic, especially if the guidewire is pulled out of the target branch vessel as well. The inherent lack of outward radial force in a self-expanding stent can make this problem worse. One particular type of self-expanding stent that has acceptable radial strength is a woven nitinol wire stent. These woven stents also have exhibit flexibility and kink resistance. However, they suffer from an extreme foreshortening on deployment. This means that they are long and small diameter in the constrained state and short with large diameter in the unconstrained state. Self-expanding stent grafts can be effective with predictable deployments when used to treat stenotic disease in the iliac and superficial femoral artery of in-stent restenosis in dialysis fistulas. But they are not designed for use in aneurysms. In the stenotic case, the walls of the stent graft are in apposition with the arterial wall along the entire length. But in an aneurysm, only the distal extent of the stent graft is in apposition with the vessel wall. So the stenotic case has much more resistance to pull out of the distal end of the stent graft than the aneurysmal case.

Yet another type of stent is a balloon-expandable stent. Balloon expandable stents are disposed on the outside of a balloon of a balloon catheter. When the balloon is inflated, it expands the stent in an outward radial direction. Without a sheath or catheter being pulled back during deployment, the positioning of the stent is predictable and there is less risk of pulling the stent graft out of its intended target vessel.

SUMMARY OF THE INVENTION

Embodiments of the bridging stent graft disclosed herein increase the predictability of the deployment location for both ends of balloon expandable stents while also providing for the kink resistance and flexibility of self-expanding stents. In particular, the bridging stent graft may be used to exclude an aneurysm from a previously deployed main body graft stent graft to a native branch vessel spanning a stent-free aneurysmal sac. Such a deployment may place new demands on small- or medium-sized stent grafts. Flexibility and conformability may be useful in such arrangements because aneurysm sacs remodel after a stent graft is implanted and blood pressure is removed from the aortic wall. This remodeling can put the bridging stents at risk of kink or crush. However, there is no arterial support along the length of the bridging stent, so accurate anchoring is desirable. Balloon expandable stents have the type of deployment mechanism necessary to achieve this type of accurate deployment. As such, the invention described herein includes a covered stent graft with balloon expandable segments on both ends to increase accuracy of stent graft placement at the intended deployement site and a self-expanding segment in the middle to increase structural integrity of the stent graft.

Thus, in a first aspect, a stent graft is provided defining a lumen having a first end and a second end, the stent graft comprising (a) a first portion at the first end of the stent graft having a first diameter and a first length, wherein a first stent structure of the first portion is balloon-expandable, (b) a second portion of the stent graft having a second diameter and a second length, wherein a second stent structure of the second portion is self-expanding, (c) a breakable restraint configured to be coupled to the second portion in a pre-deployment state and decoupled from the second portion in a deployed state, and (d) a third portion at the second end of the stent graft has a third diameter and a third length, wherein a third stent structure of the third portion is balloon-expandable.

In a second aspect, the present invention provides a method comprising: (a) introducing a guidewire into an arterial configuration via arterial access, (b) loading a delivery catheter containing the stent graft of the first aspect onto the guidewire, (c) moving the delivery catheter along the guidewire and introducing the delivery catheter into the arterial configuration via arterial access, and (d) deploying the stent graft into at least one of the arterial configuration and a lumen of a previously-placed stent graft.

These as well as other aspects, advantages, and alternatives, will become apparent to those of ordinary skill in the art by reading the following detailed description, with reference where appropriate to the accompanying drawings.

DETAILED DESCRIPTION OF THE INVENTION

Figure 1:
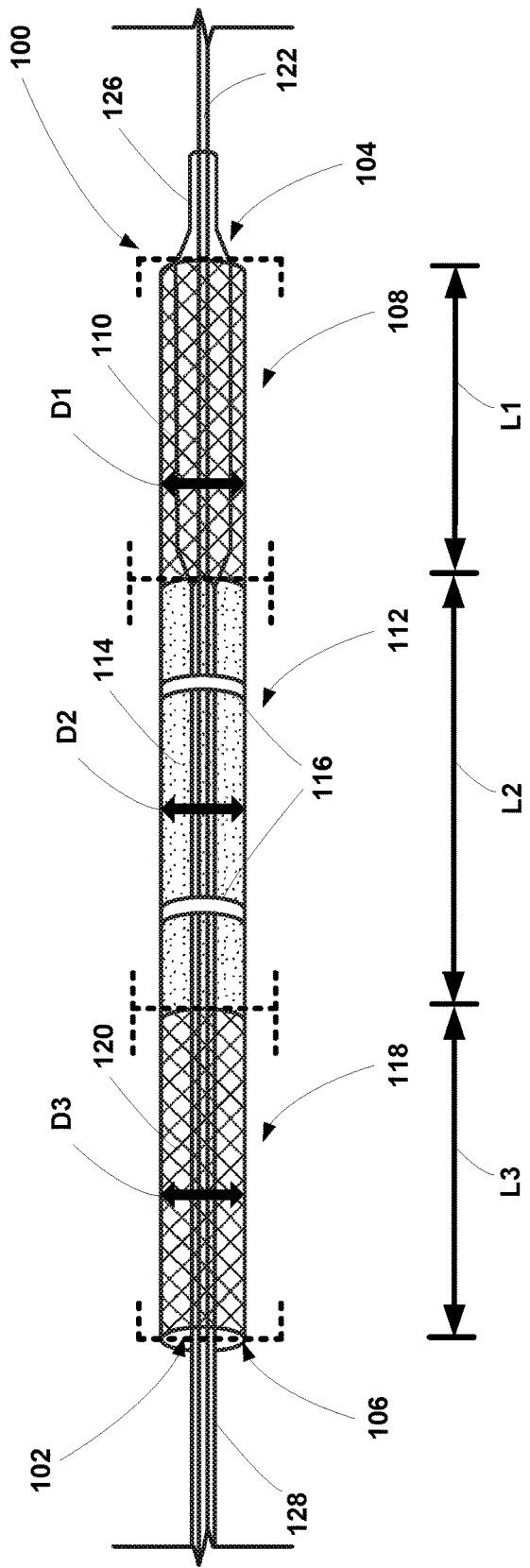
FIG. 1 shows a side perspective view of a stent graft in a pre-deployment state, according to an example embodiment.

Exemplary stent grafts and methods are described herein. It should be understood that the word "exemplary" is used herein to mean "serving as an example, instance, or illustration." Any embodiment or feature described herein as "exemplary" is not necessarily to be construed as preferred or advantageous over other embodiments or features. The exemplary embodiments described herein are not meant to be limiting. It will be readily understood that certain aspects of the disclosed systems and methods can be arranged and combined in a wide variety of different configurations, all of which are contemplated herein.

Furthermore, the particular arrangements shown in the Figures should not be viewed as limiting. It should be understood that other embodiments may include more or less of each element shown in a given Figure. Further, some of the illustrated elements may be combined or omitted. Yet further, an exemplary embodiment may include elements that are not illustrated in the Figures.

As used herein, with respect to measurements, "about" means+/−5%.

As used herein, diameter ranges pertain to an unconstrained, ex vivo state of the stent graft and stent graft extensions. When the stent graft and stent graft extensions are in a constrained, in vivo state the diameter ranges will be on the order of about 10-20% smaller in diameter than the unconstrained, ex vivo state.

As used herein, "second end" refers to the end of the main body stent graft that will be a "distal end" upon deployment in vivo through which blood flow exits the lumen of the stent graft.

As used herein, "passive fixation" refers to friction, interaction between the cloth of the grafts, radial strength of the stent structure and blood pressure that holds the component stent grafts together at the site of overlap.

As used herein, "active fixation" refers to features coupled to a stent, graft, or stent graft that may actively engage vasculature or another stent graft, including hooks, bi-directional hooks, stent structure elements, anchors, staples, bio-activated adhesive, or a combination thereof, among other possibilities.

As used herein, "string" refers to a low-friction material such as GORE-TEX Suture for example.

As used herein, "foreshortening" refers to the change in shape a stent undergoes upon deployment, typically involving the stent being shortened and having a larger diameter in the unconstrained state and being longer and having a smaller diameter in the constrained state. Typically woven nitinol stents experience significant foreshortening while laser-cut nitinol stents experience minimal foreshortening upon deployment.

As used herein, a "stent graft" is a tubular, radially-expandable device comprising a fabric supported by a stent, and may be used to bridge aneurysmal arteries. As such, the term stent graft may be used herein to include bridging stent grafts. Such stent grafts and methods for their deployment and use are known to those of skill in the art. For example, vascular sheaths can be introduced into the patient's arteries, through which items, including but not limited to, guidewires, catheters and, eventually, the stent graft, may be passed.

As used herein, a "stent" is typically a cylindrical frame and means any device or structure that adds rigidity, expansion force, or support to a prosthesis, while "stent graft" refers to a prosthesis comprising a stent and a graft material associated therewith that forms a lumen through at least a portion of the length of the stent. A "graft" is a cylindrical liner that may be disposed on the stent's interior, exterior or both. A wide variety of attachment mechanisms are available to join the stent and graft together, including but not limited to, sutures, adhesive bonding, heat welding, and ultrasonic welding.

The stent can be made of any suitable material, including but not limited to biocompatible metals, implantable quality stainless steel wires, nickel and titanium alloys, and biocompatible plastics. The stents can either have material properties necessary to exhibit either self-expanding or balloon-expanding characteristics.

Any suitable graft material can be used. In a preferred embodiment, the graft material is a biocompatible fabric, including but not limited to woven or knitted polyester, such as poly(ethylene terephthalate), polylactide, polyglycolide and copolymers thereof; fluorinated polymers, such as PTFE, expanded PTFE and poly(vinylidene fluoride); polysiloxanes, including polydimethyl siloxane; and polyurethanes, including polyetherurethanes, polyurethane ureas, polyetherurethane ureas, polyurethanes containing carbonate linkages and polyurethanes containing siloxane segments. Materials that are not inherently biocompatible may be subjected to surface modifications in order to render the materials biocompatible. Examples of surface modifications include graft polymerization of biocompatible polymers from the material surface, coating of the surface with a crosslinked biocompatible polymer, chemical modification with biocompatible functional groups, and immobilization of a compatibilizing agent such as heparin or other substances. The graft material may also include extracellular matrix materials.

As used herein, a "catheter" is an apparatus that is connected to a deployment mechanism and houses a medical device that can be delivered over a guidewire. The catheter may include a guidewire lumen for over-the-wire guidance and may be used for delivering a stent graft to a target lumen. A catheter can have braided metal strands within the catheter wall for structural improvements. The structural elements of the catheter tip can be bonded or laser welded to the braided strands of the catheter to improve the performance characteristics of the catheter tip.

As used herein, a "guidewire" is an elongated cable comprised of various biocompatible materials including metals and polymers. Guidewires may be used for selecting target lumens and guiding catheters to target deployment locations. Guidewires are typically defined as wires used independently of other devices that do not come as part of an assembly.

As used herein, "lumen" refers to a passage within an arterial structure, such as the pulmonary arteries, or stent grafts or the passage within the tubular housings or catheters through which the guidewire may be disposed.

As used herein, "deployment" refers to when the stent graft has been positioned in the target lumen and is actively being expanded.

With reference to the Figures, FIG. 1 illustrates a stent graft 100 in a compressed pre-deployment state. The compressed pre-deployment state is used during delivery of the stent graft 100 to the target lumen. The stent graft 100 defines a lumen 102 having a first end 104 and a second end 106. The stent graft 100 includes a first portion 108 at the first end 104 of the stent graft 100 having a first diameter D1 and a first length L1. Further, the stent graft 100 includes a first stent structure 110 arranged in the first portion 108 that is balloon-expandable. Such a balloon-expandable stent structure may advantageously enable a user to improve accuracy of the deployment location of the stent graft 100. In one example, the material of the first stent structure 110 may include 316L stainless steel, a cobalt-chromium alloy (MP35N and L-605), a platinum-chromium alloy, a platinum-iridium alloy, a titanium alloy (Ti-6Al-4V and CP titanium), Tantalum, a Niobium alloy, Poly-L-lactic acid (PLLA), and/or a magnesium alloy.

When the balloon 126 is inflated, it expands the stent graft 100 in an outward radial direction. Without a sheath or catheter being pulled back during deployment, the positioning of the stent graft 100 is predictable and there is less risk of pulling the stent graft out of its intended target vessel.

The stent graft 100 also includes a second portion 112 of the stent graft 110 having a second diameter D2 and a second length L2. The stent graft 100 further includes a second stent structure 114 arranged in the second portion 112 that is self-expanding. Self-expanding stents can make bends as they change directions from the main body stent graft to the target branch vessel, and may also exhibit kink resistance. As such, in the event that the aneurysm remodels, the self-expanding stent may avoid kinking and ultimately occluding in addition to allowing some compliance to the remodeling.

The stent graft 100 also includes a third portion 118 at the second end 106 of the stent graft 100 having a third diameter D3 and third length D3. The stent graft 100 further includes a third stent structure 120 arranged in the third portion 118 that is balloon-expandable. In one example, the material of the first stent structure 110 may include 316L stainless steel, a cobalt-chromium alloy (MP35N and L-605), a platinum-chromium alloy, a platinum-iridium alloy, a titanium alloy (Ti-6Al-4V and CP titanium), Tantalum, a Niobium alloy, Poly-L-lactic acid (PLLA), and/or a magnesium alloy. In one example, the material of the third stent structure 120 is the same as the material of the first stent structure 110. In another example, the material of the third stent structure 120 is different than the material of the first stent structure 110. As shown in FIG. 1, the second portion 112 may be arranged between the first portion 108 and the third portion 118 of the stent graft 100. As discussed above, a balloon-expandable stent structure may advantageously enable a user to improve accuracy of the deployment location of the stent graft 100.

Figure 3:
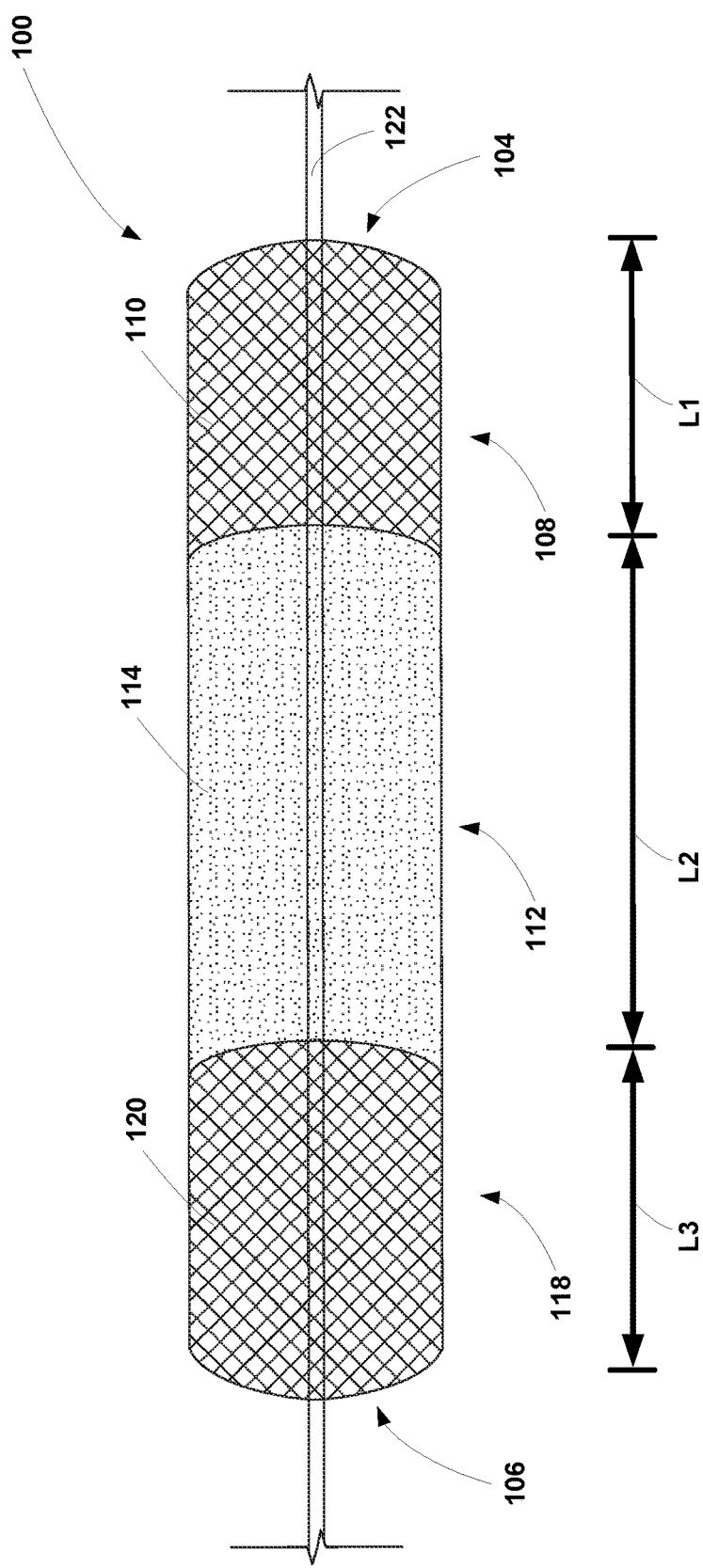
FIG. 3 shows a side perspective view of the stent graft in a fully deployed state, according to an example embodiment.

The stent graft 100 also includes a breakable restraint 116 configured to be coupled to the second portion 112 in the pre-deployment state (see FIG. 1) and decoupled from the second portion 112 in a deployed state (see FIG. 3). The breakable restraint 116 may comprise one of at least one polymer band, a polymer mesh, at least one biocompatible string, at least one cloth band, or a fracture point in the self-expanding stent structure. The breakable restraint 116 may help maintain the second portion 116 in the compressed pre-deployment position during stent graft delivery to the target location. The breakable restraint 116 may then be removed prior to or during expansion of the second portion 116. In one example, when the breakable restraint 116 is broken, the breakable restraint 116 is still partially coupled to the second portion 112 of the stent graft 100. In another example, when the breakable restraint 116 is broken, the breakable restraint 116 is completely removed from contact with the second portion 112 of the stent graft 100.

In one example, each of the first, second and third diameters D1, D2, D3 may range from about 4 mm to about 30 mm in an ex vivo expanded condition. In another example, each of the first, second and third lengths L1, L2, L3 may range from about 20 mm to about 250 mm in the ex vivo expanded condition. As such, the total length of the stent graft 100 may range between about 60 mm long to about 750 mm long. In one example, each of the first diameter D1, the second diameter D2, and the third diameter D3 are the same. In another example, the first diameter D1 and the third diameter D3 are equal, and the second diameter D2 is different than the first diameter D1 and the third diameter D3. In particular, the second diameter D2 may be less than the first and third diameters D1, D3 to help ensure that the stent graft 100 is properly anchored in the target lumen upon deployment. For example, since the second portion 112 may be arranged to span an aneurysm, it may be advantageous for the second diameter D2 to be less than the first and third diameters D1, D3 to reduce pressure on the aneurysmal wall from the stent graft 100. In one example, each of the first length L1, the second length L2, and the third length L3 are different. In another example, the first length L1 and the third length L3 are equal, and the second length L2 is different than the first length L1 and the third length L3. In one example, the second length L2 is greater than both the first length L1 and the third length L3. For example, the second length L2 may be at least about 1.5 times greater than the first length L1 and the third length L3. In another example, the second length L2 is less than both the first length L1 and the third length L3.

Figure 2C:
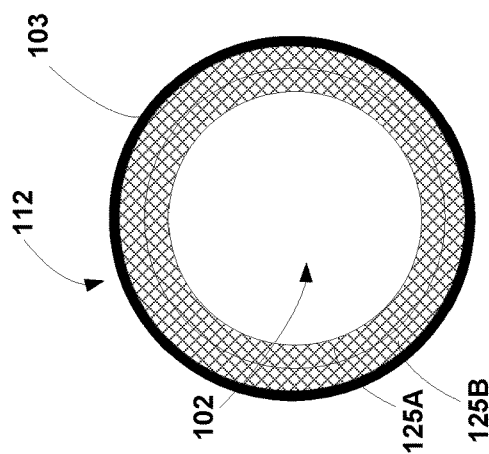
FIG. 2C shows a front cross-section view of the section portion of the stent graft, according to an example embodiment.
Figure 2B:
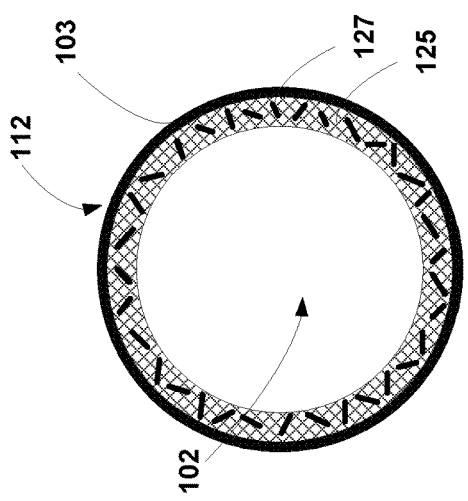
FIG. 2B shows a front cross-section view of the second portion of the stent graft, according to an example embodiment.
Figure 2A:
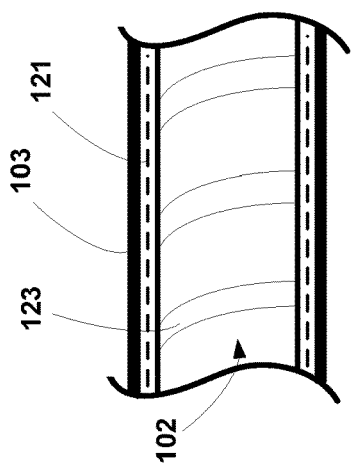
FIG. 2A shows a side cross-section view of the stent graft, according to an example embodiment.

In one example, as shown in FIG. 2A, a plurality of expandable filaments 121 may be woven through the first, second and third stent structures 110, 114, 120. In such an example, the plurality of expandable filaments may be configured to expand within the stent structure 110, 114, 120 upon exposure to blood or to a reactant chemical. Further, the plurality of expandable filaments 121 may be woven in a direction of blood flow from the first end 104 of the stent graft 100 to the second end 106 of the stent graft 100. In another embodiment, a surface of the lumen 102 may include helical grooves 123. Such helical grooves 123 may assist in encouraging a helical flow directing inner surface (e.g., rifling) that may allow the blood flow to mature in a shorter distance. This may beneficially encourage healthier flow distal to the stent graft 100 which would encourage an increase in long term patency and durability.

Further, as shown in FIG. 2B, the second stent structure 114 may comprise a plurality of woven nitinol wires 125. In such an example, the second stent structure 114 may further comprise textile fibers 127 intermixed within the woven nitinol wires 125. In particular, textile fibers 127 can be woven into the nitinol weave in opposing winds. The mix of the two can be optimized in such a way as to match the stretch and compliance of the artery it is supposed to replace. In addition, the outer surface of the second stent structure 114 can be woven in such a way as to create a wear surface and discourage tissue ingrowth. The inner surface of the second stent structure 114 can be woven in such a way as to encourage tissue ingrowth to create the process of endothelization. If the textile fibers 127 on the inner surface of the second stent structure 114 are woven in such a way as to align with the direction of blood flow it can further encourage endothelialization. For example, the textile fibers 127 may expand when exposed to blood or when exposed to a second component for a binary polymer (e.g., growing a polymer on the stent structure), thereby filling in any gaps within the stent structure.

In another example, the second stent structure 114 further may further comprise a polymer material intermixed within the woven nitinol wires 125. In yet another example, as shown in FIG. 2C, the second stent structure 114 comprises a plurality of layers of woven nitinol wires 125A, 125B. Further, the stent graft 100 may include a graft cover 103 positioned on an outer surface of the stent graft 100. Similar to the woven nature of the second stent structure 114, the graft cover 103 may be woven in such a way that, if placed on the outer surface of the stent graft 100, the graft cover 103 may encourage cellular ingrowth. This may further improve tissue ingrowth from the native branch vessel to the graft cover 103.

In one example, a stiffness of the third stent structure 120 is greater than a stiffness of the first stent structure 110, and the stiffness of the first stent structure 110 is greater than a stiffness of the second stent structure 114. In such an example, the first stent structure 110 may comprise a first material, the second stent structure 114 may comprise a second material, and the third stent structure 120 may comprise a third material, such that each of the first material, the second material, and the third material are different from each other. In another optional example, the material of the first stent structure 110 has a first thickness, the material of the second stent structure 114 has a second thickness, and the material of the third stent structure 120 has a third thickness, such that each of the first thickness, the second thickness, and the third thickness are different from each other.

As such, the first end 104 of the stent graft 100 may be more compliant and the second end 106 more stiff. The stiffer second end 106 may provide a firmer location for receiving the end of another bridging stent or for itself to firmly fit within another previously-deployed stent graft. The more compliant first end 104 can either conform to an adjoining previously deployed stent or stent graft or mate with the native branch vessel with a compliance that more closely matches the native tissue. Stent graft compliance similar to the native tissue may reduce stenosis, because if the stent graft 100 is significantly stiffer than the target branch artery, the result may be that the native tissue stretches causing micro trauma in the branch artery distal to the bridging stent that may in turn cause stenosis.

In operation, an example method may include (a) introducing a guidewire 122 into an arterial configuration via arterial access, (b) loading a delivery catheter 124 containing the stent graft 100 according to the embodiments described above onto the guidewire 122, (c) moving the delivery catheter 124 along the guidewire 122 and introducing the delivery catheter 124 into the arterial configuration via arterial access, and (d) deploying the stent graft 100 into at least one of the arterial configuration and a lumen of a previously-placed stent graft.

In one embodiment, the method may further include (e) expanding a balloon 126 in each of the first portion 108 of the stent graft 100, the third portion 118 of the stent graft 100, and the second portion 112 of the stent graft 100 to thereby break the breakable restraint 116.

FIGS. 1 and 3 illustrate the various steps of the method described above. In particular, FIG. 1 illustrates the stent graft 100 in a pre-deployment position as delivered to the target location, over the balloon catheter 128 with the balloon 126 of the balloon catheter 128 being disposed within the first potion 108 of the stent graft 100. Once the stent graft 100 is positioned in the desired target location, the balloon 126 may be inflated in the stent graft 100. The balloon-expandable structures 110, 120 allow for precise delivery and anchoring in the target branch vessel, another previously-deployed bridging stent graft, or a previously-deployed main body stent graft. In one embodiment, inflating the balloon 126 may break the breakable restraint 116 and release the self-expandable second stent structure 114 of the stent graft 100, as shown in FIG. 3.

In another embodiment, the method may further include (h) positioning an infusion catheter in second portion 112 of the stent graft 100, and (i) providing a flowable polymer to the second portion 112 of the stent graft 100. A compliant cover for the stent is preferred to accommodate a change in shape that a woven stent undergoes when going from a constrained position to an unconstrained. Currently known graft covers (expanded PTFE or polyester) may be used, but further compliance may be achieved through unique delivery techniques. for example, one advantageous delivery method may include adding the graft cover to the inner surface of the stent in the patient in vivo. If woven nitinol serves as a base structure or scaffold of a stent, a flowable material could be added after the bare metal stent was in place. For example, the woven scaffold of wires can be filled with a flowable polymer material. Once the nitinol scaffold is in place, an infusion catheter can be guided to be within the woven nitinol structure and the polymer can be infused along the surface of the nitinol scaffold. The polymer can fill the pores of the nitinol scaffold so as to prevent an endoleak and ultimately pressurization of the aneurysmal sac.

It will be appreciated that other arrangements are possible as well, including some arrangements that involve more or fewer steps than those described above, or steps in a different order than those described above.

While various aspects and embodiments have been disclosed herein, other aspects and embodiments will be apparent to those skilled in the art. All embodiments within and between different aspects of the invention can be combined unless the context clearly dictates otherwise. The various aspects and embodiments disclosed herein are for purposes of illustration and are not intended to be limiting, with the true scope and spirit being indicated by the claims.

The invention claimed is:

1. A stent graft defining a lumen having a first end and a second end, comprising:
   a first portion at the first end of the stent graft having a first diameter and a first length, wherein a first stent structure of the first portion is balloon-expandable;
   a second portion of the stent graft having a second diameter and a second length, wherein a second stent structure of the second portion is self-expanding;
   a breakable restraint coupled to the second portion in a pre-deployment state and configured to be decoupled from the second portion in a deployed state;
   a third portion at the second end of the stent graft having a third diameter and a third length, wherein the second portion is arranged between the first portion and the third portion of the stent graft, wherein a third stent structure of the third portion is balloon-expandable, wherein a stiffness of the third stent structure is greater than a stiffness of the first stent structure, and wherein the stiffness of the first stent structure is greater than a stiffness of the second stent structure; and a plurality of expandable filaments woven through the first stent structure, the second stent structure and the third stent structure, wherein the plurality of expandable filaments are woven from the first end of the stent graft to the second end of the stent graft in a direction of blood flow, and wherein the plurality of expandable filaments are configured to expand within the stent structure upon exposure to blood or a reactant chemical.

2. The stent graft of claim 1, wherein each of the first diameter, the second diameter and the third diameter ranges from about 4 mm to about 30 mm.

3. The stent graft of claim 1, wherein each of the first length, the second length and the third length range from about 20 mm to about 250 mm.

4. The stent graft of claim 1, wherein the breakable restraint comprises one of at least one polymer band, a polymer mesh, at least one biocompatible string, at least one cloth band, or a fracture point in the second stent structure.

5. The stent graft of claim 1, wherein the first stent structure comprises a first material, wherein the second stent structure comprises a second material, wherein the third stent structure comprises a third material, and wherein each of the first material, the second material, and the third material are different from each other.

6. The stent graft of claim 5, wherein the first material of the first stent structure has a first thickness, wherein the second material of the second stent structure has a second thickness, wherein the third material of the third stent structure has a third thickness, and wherein each of the first thickness, the second thickness, and the third thickness are different from each other.

7. The stent graft of claim 5, wherein the second material comprises a plurality of woven nitinol wires.

8. The stent graft of claim 7, wherein the second material further comprises textile fibers intermixed within the woven nitinol wires.

9. The stent graft of claim 7, wherein the second material further comprises a polymer material intermixed within the woven nitinol wires.

10. The stent graft of claim 5, wherein the second material comprises a plurality of layers of woven nitinol wires.

11. The stent graft of claim 1, further comprising helical grooves along an inner surface of the stent graft.

12. The stent graft of claim 1, further comprising a stent graft cover positioned on an outer surface of the stent graft.

13. The stent graft of claim 1, wherein each of the first diameter, the second diameter, and the third diameter are the same.

14. The stent graft of claim 1, wherein the first diameter and the third diameter are equal, and the second diameter is different than the first diameter and the third diameter.

15. The stent graft of claim 1, wherein each of the first length, the second length, and the third length are different from each other.

16. The stent graft of claim 1, wherein the first length and the third length are equal, and the second length is different than the first length and the third length.

17. A method for placement of a stent graft, the method comprising:
introducing a guidewire into an arterial configuration via arterial access;
loading a delivery catheter containing the stent graft according to claim 1 onto the guidewire;
moving the delivery catheter along the guidewire and introducing the delivery catheter into the arterial configuration via arterial access; and
deploying the stent graft into at least one of the arterial configuration and a lumen of a previously-placed stent graft.

18. The method of claim 17, further comprising:
expanding a balloon in each of the first portion of the stent graft, the third portion of the stent graft, and the second portion of the stent graft to thereby break the breakable restraint.

19. The method of claim 17, further comprising:
positioning an infusion catheter in the second portion of the stent graft; and
providing a flowable polymer to the second portion of the stent graft.

* * * * *